US 10,029,126 B2

(12) United States Patent
Carol et al.

(10) Patent No.: US 10,029,126 B2
(45) Date of Patent: Jul. 24, 2018

(54) SYSTEM AND METHOD OF DELIVERING FOCUSED ULTRASOUND TREATMENT USING A VARIABLE VOLUME FLUID BLADDER

(71) Applicant: SONACARE MEDICAL, LLC, Charlotte, NC (US)

(72) Inventors: Mark Carol, Charlotte, NC (US); Robert D. Parks, Charlotte, NC (US); Robert Craig Campbell, Charlotte, NC (US); Drew T. Degentesh, Charlotte, NC (US)

(73) Assignee: SONACARE MEDICAL, LLC, Charlotte, NC (US)

( * ) Notice: Subject to any disclaimer, the term of this patent is extended or adjusted under 35 U.S.C. 154(b) by 159 days.

(21) Appl. No.: 15/027,061

(22) PCT Filed: Oct. 10, 2014

(86) PCT No.: PCT/US2014/060087
§ 371 (c)(1),
(2) Date: Apr. 4, 2016

(87) PCT Pub. No.: WO2015/054605
PCT Pub. Date: Apr. 16, 2015

(65) Prior Publication Data
US 2016/0236013 A1 Aug. 18, 2016

Related U.S. Application Data

(60) Provisional application No. 61/889,907, filed on Oct. 11, 2013.

(51) Int. Cl.
A61N 7/02 (2006.01)
A61B 18/04 (2006.01)
(Continued)

(52) U.S. Cl.
CPC ............... *A61N 7/02* (2013.01); *A61B 18/04* (2013.01); *A61B 2017/2253* (2013.01);
(Continued)

(58) Field of Classification Search
CPC ............ A61B 18/04; A61B 2017/2253; A61B 2018/00023; A61B 2018/00577;
(Continued)

(56) References Cited

U.S. PATENT DOCUMENTS 5,601,526 A 2/1997 Chapelon et al.
7,559,905 B2 7/2009 Kagosaki et al.
(Continued)

OTHER PUBLICATIONS

Supplementary European Search Report, dated Mar. 8, 2017, in corresponding European Patent Application No. 4851897.
(Continued)

Primary Examiner — Ruth S Smith
(74) Attorney, Agent, or Firm — Mark T. Vogelbacker; Eckert Seamans Cherin & Mellott LLC

(57) ABSTRACT

A system for providing focused ultrasound may include a focused ultrasound probe including at least one transducer. At least one variable volume fluid bladder may be positioned between at least a portion of the transducer and tissue to be treated. The system may further include a reservoir containing fluid and a first pump operatively connected to the bladder and the reservoir. The first pump may be configured to move fluid into the bladder. A second pump may be operatively connected to the bladder and the reservoir. The second pump may be configured to move fluid out of the bladder.

19 Claims, 3 Drawing Sheets

(51) Int. Cl.
  *A61B 18/00* (2006.01)
  *A61N 7/00* (2006.01)
  *A61B 17/225* (2006.01)

(52) U.S. Cl.
  CPC ............... *A61B 2018/00023* (2013.01); *A61B 2018/00577* (2013.01); *A61B 2018/00642* (2013.01); *A61B 2018/00738* (2013.01); *A61B 2018/00744* (2013.01); *A61B 2018/00863* (2013.01); *A61N 2007/0056* (2013.01); *A61N 2007/0091* (2013.01)

(58) Field of Classification Search
  CPC  A61B 2018/00642; A61B 2018/00738; A61B 2018/00744; A61B 2018/00863; A61N 2007/0056; A61N 2007/0091; A61N 7/02
  See application file for complete search history.

(56) References Cited

U.S. PATENT DOCUMENTS

| | | |
|---|---|---|
| 7,722,839 B2 | 5/2010 | Kuzyk |
| 2003/0060813 A1 | 3/2003 | Loeb et al. |
| 2007/0066897 A1 | 3/2007 | Sekins et al. |
| 2010/0240002 A1 | 9/2010 | Halevy-Politch et al. |
| 2013/0165823 A1 | 6/2013 | Ishibashi et al. |
| 2013/0248446 A1 | 9/2013 | Frugier |

OTHER PUBLICATIONS

International Search Report for PCT/US2014/060087, dated Jan. 29, 2015.
International Preliminary Report on Patentability for PCT/US2014/060081, dated Feb. 19, 2016.

SYSTEM AND METHOD OF DELIVERING FOCUSED ULTRASOUND TREATMENT USING A VARIABLE VOLUME FLUID BLADDER

CROSS-REFERENCE TO RELATED APPLICATION

This application is the United States national stage application of International Application No. PCT/US2014/060087, filed Oct. 10, 2014, which claims benefit of U.S. Provisional Application No. 61/889,907, filed Oct. 11, 2013, both of which are herein incorporated by reference in their entirety.

SUMMARY

The present disclosure is generally directed to focused ultrasound ("FUS") devices for therapeutic intervention using ultrasound ("US") transducers to deliver a generally thermal or cavitational dose to a small, well-defined location at some fixed or focal distance from the transducer surface. One or more ultrasound crystals may be combined to form a transducer that can be geometrically and/or electronically focused at a point distant or spaced-apart from the surface of the transducer, thereby concentrating the US energy at the focal spot. This concentration of sound energy results in cavitational and thermal damage or therapy to the region of focus (e.g., patient tissue) and can be used, among other things, to destroy cancerous tissue.

In order to treat volumes of tissue larger than the volume of the focal spot of the transducer(s), the focal spot of the transducer(s) may be moved so that the small spot of thermal dose is scanned over the region that is to receive thermal or cavitational dose. Alternatively, the patient can be moved relative to the transducer. The latter approach is often used in extracorporeal devices where the transducer is located outside the patient. Such is the case with the SonaCare Medical, Inc. EXABLATE™ system. The former approach is used often in devices where the transducer is located inside the patient. Such is the case with devices such as the SonaCare Medical, Inc. SONATHERNM™ and SONABLATE™ devices.

Regardless, the depth of the focal spot in a tissue region may need to be adjusted so as to treat volumes of tissue at varying depth inside a patient or an organ or volume of tissue inside a patient. One way for doing this involves electronically refocusing the transducer so that the focal spot occurs at varying depth. This requires multiple crystals arranged in a linear, annular, or matrix manner each of which can have its phase altered electronically, thereby allowing peaks of intensity to overlap at varying points in space. This approach is expensive in terms of crystals, electronic circuits, and may require space larger than that which may be provided in a probe that is to be introduced into a patient.

Another approach to varying depth of delivery is mechanical in nature. Most HIFU ("high intensity, focused ultrasound") systems typically include a means for coupling the transducer(s) to the tissue to be treated. Coupling can involve providing a continuous water path between the transducer and the tissue being treated. This coupling mechanism can be used to control the depth of the focal point of the transducer in the region of interest; increasing the depth of the water enclosed in the means for coupling moves the focal point of the transducer closer to the surface of the volume of tissue being treated, decreasing the amount of water moves the focal spot deeper into the tissue to which it is coupled. Such systems are used typically with invasive systems often due to space constraints. Mechanical systems of this type are labor and time intensive. Adjustments in depth are made based on user review of imaging information or plans generated by a treatment planning system that then requires user interaction to execute and may involve manual trial and error injection or removal of water from the means for coupling. This introduces time, labor; and potential for error in the delivery of the HIFU treatment.

In addition, fluid is used for another purpose other than just to control tissue contact, namely to control temperature. The process of delivering FUS (focused ultrasound) therapy requires the generation of high levels of heat at the transducer surface due to inefficiency in the ability of the transducer to convert electrical energy to mechanical vibrations. This heat must be removed from the surface of the transducer or the transducer may fail. The most common way to do this is to circulate water, which may be cooled, around the transducer. This circulation requires a pumping system and fluid path connections in addition to those used to allow fluid to be injected around the transducer in order to create tissue contact.

Therefore, it is desirable to provide a means of circulating fluid around a FUS transducer and varying the depth of the focal spot of a transducer inside a patient without requiring complicated crystal and electronics design or multiple fluid pathways.

In one embodiment, the present disclosure includes a means for providing water circulation around FUS transducer as well automatic depth adjustment of the focal spot of a FUS system in order to move the focal spot of a HIFU probe around in the z-axis without the need for an array-type transducer. The means for providing water circulation includes a variable volume fluid bladder integrated into or brought in contact with the probe. The bladder may be connected to two pumps, one of which is set-up to cause fluid to flow into the bladder and one of which is setup to cause fluid to flow out of the bladder. Both pumps may be connected also to a common reservoir. By varying under computer or user control the relative speeds of the two pumps, the amount of water flowing into/out of the bladder can be varied, thereby increasing or decreasing the volume of fluid inside the bladder, which in turn changes the depth in tissue of the focal spot of the probe containing the transducer, all the while circulating continuously fluid around the transducer.

In a further embodiment of the present disclosure, the speed of each pump can be controlled manually by keys or buttons or can be controlled automatically by a computer system that executes a predetermined treatment plan or that adjusts each pump automatically in order to compensate for changes in tissue volumes or in the location of volumes that occur as a result of biological, interventional, or other activities.

In another embodiment of the present disclosure, the system may include a mechanical means for measuring the amount of fluid in the bladder and/or in the fluid reservoir or may determine the amount of fluid in the bladder and/or reservoir through means associated with the analysis of medical imaging of the tissue volume or weights or volumes of fluid flowing through each of the two pumps, thereby providing a feedback loop that allows the volume to be kept constant or to be varied as indicated by the clinical situation.

The present disclosure also includes a method of delivering a FUS treatment. The method includes the steps of: equipping a HIFU device with a variable volume bladder to be interposed between the device and tissue containing the volume of tissue to be treated; connecting the bladder to two pumping systems, one of which causes fluid to flow into the bladder, one of which causes fluid to flow out of the bladder, each pump connected also to a common reservoir of fluid; varying the speed of the two pumps relative to each other thereby controlling circulation of fluid around the PUS transducer and the volume of fluid in the bladder thereby positioning the focal spot of the transducer in the z-plane.

An additional method of delivering a FUS treatment is provided. The method includes the steps of: equipping a HIFU device with a variable volume bladder to be interposed between the device and tissue containing the volume of tissue to be treated; connecting the bladder to two pumping systems, one of which causes fluid to flow into the bladder, one of which causes fluid to flow out of the bladder, each pump connected also to a common reservoir of fluid; varying the speed of the two pumps relative to each other under computer control, the control consisting of keys or other means of computer input thereby controlling circulation of fluid around the FUS transducer while providing the user with the ability to control the volume of fluid in the bladder and in turn the location of the focal spot in the z-plane.

A further method of delivering a FUS treatment is provided. The method includes the steps of: equipping a HIFU device with a variable volume bladder to be interposed between the device and tissue containing the volume of tissue to be treated; connecting the bladder to two pumping systems, one of which causes fluid to flow into the bladder, one of which causes fluid to flow out of the bladder, each pump connected also to a common reservoir of fluid; varying the speed of the two pumps relative to each other under computer control, the control consisting of automatic adjustment of pump speed without direct user input controlling circulation of fluid around the FUS transducer while allowing control of the volume of fluid in the bladder and in turn the location of the focal spot in the z-plane.

DRAWINGS

The foregoing summary, as well as the following detailed description of the invention, will be better understood when read in conjunction with the appended drawings. For the purpose of illustrating the invention, there are shown in the drawings various illustrative embodiments. It should be understood, however, that the invention is not limited to the precise arrangements and instrumentalities shown.

DETAILED DESCRIPTION

Figure 1A:
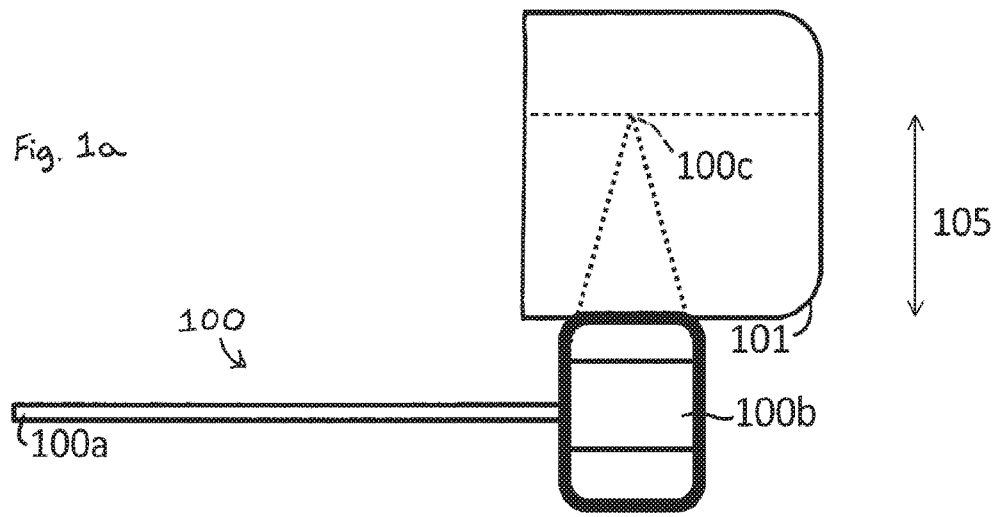
FIG. 1a is an elevational view of a combination transducer and bladder according to an embodiment of the present disclosure, wherein the relative small bladder provides a relatively great depth of a focal spot.

Various embodiments of the present disclosure are described hereinafter with reference to the figures. It should be noted that the figures are not drawn to scale and elements of similar structures or functions are represented by like reference numerals throughout the figures. It should also be noted that the figures are not intended to facilitate the description of specific embodiments of the invention. The figures are not intended as an exhaustive description of the invention or as a limitation on the scope of the invention. In addition, an aspect described in conjunction with a particular embodiment of the present invention is not necessarily limited to that embodiment and can be practiced in any other embodiments of the present invention. It will be appreciated that while various embodiments of the invention are described in connection with radiation treatment of tumors, the claimed invention has application in other industries and to targets other than cancers. Unless specifically set forth herein, the terms "a," "an" and "the" are not limited to one element, but instead should be read as "at least one."

The present disclosure includes a system for providing focused ultrasound that includes a focused ultrasound probe with at least one transducer. At least one variable volume fluid bladder may be positioned between at least a portion of the transducer and tissue to be treated. The system may further include a reservoir containing fluid and a first pump operatively connected to the bladder and the reservoir. The first pump may be configured to move fluid into the bladder. A second pump may be operatively connected to the bladder and the reservoir. The second pump may be configured to move fluid out of the bladder.

The present disclosure also includes a method of delivering focused ultrasound treatment that includes placing a variable volume fluid bladder between at least a portion of a transducer of a focused ultrasound device and tissue to be treated. The bladder may be operatively connected to a first pump and a second pump. The method may further includes varying an operating speed of at least one of the first pump and the second pump to (i) control circulation of fluid around or near at least a portion of the transducer and (ii) adjust a position of a focal spot of the transducer.

Figure 1B:
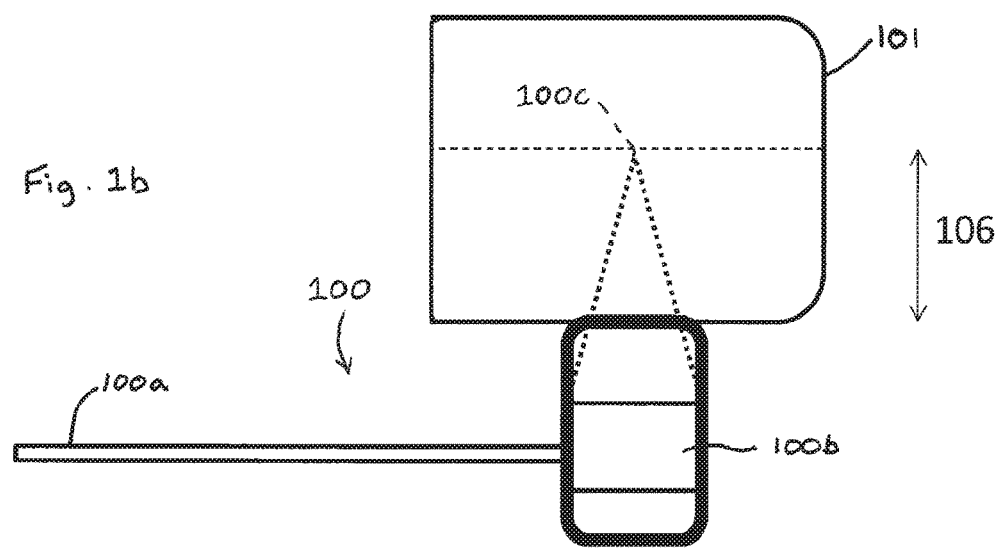
FIG. 1b is another elevational view of the combination shown in FIG. 1a, wherein the bladder of intermediate volume provides an intermediate depth of the focal spot.
Figure 1C:
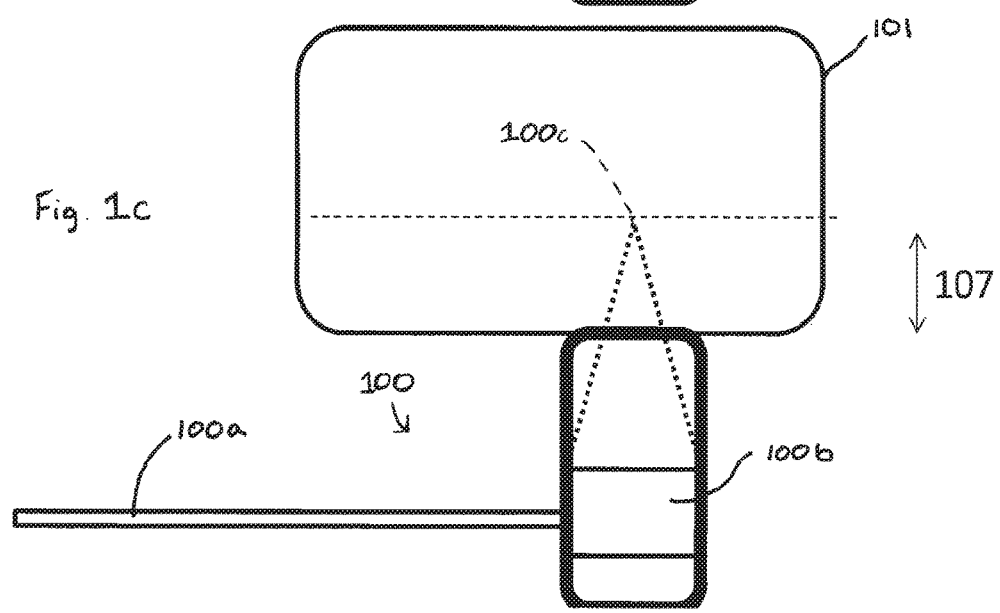
FIG. 1c is another elevational view of the combination shown in FIG. 1a, wherein the bladder with a relatively large volume provides a relatively small depth of the focal spot.

More particularly, in one embodiment as depicted in FIGS. 1a-1c, one or more fixed focal spot transducers 100b designed to deliver FUS may be fixedly or removably secured to a rigid or flexible shaft 100a. In combination, the transducer(s) 100b and the shaft 100a constitute a therapy probe, generally designated 100. The transducer(s) 100b may be positioned at or near a distal end of the shaft 100a. In operation, the transducer(s) 100b produces a focal spot 100c. As understood by those skilled in the art, an imaging US transducer can be mounted in proximity to therapy transducers as part of the probe 100.

An elastic, flexible and/or variable fluid bladder 101 may be secured to at least a portion (e.g., the distal end) of the probe 100 in a permanent or removable manner. The bladder 101 may be formed of any material, such as a flexible polymeric material, that is not tissue reactive and can expand as needed. The bladder 101 includes a cavity that is fillable with fluid, such as water. In one embodiment, the bladder 101 may include a non-distensible section surrounding at least a portion of the probe's shaft 100a and/or the transducer(s) 100b, and an inflatable or distensible portion, that can be enlarged in size by the injection of fluid and/or reduced in size by removal of the fluid. In one embodiment, the bladder 101 encloses at a minimum the transducer section of the probe 100.

Figures 2A, 2B, 2C:
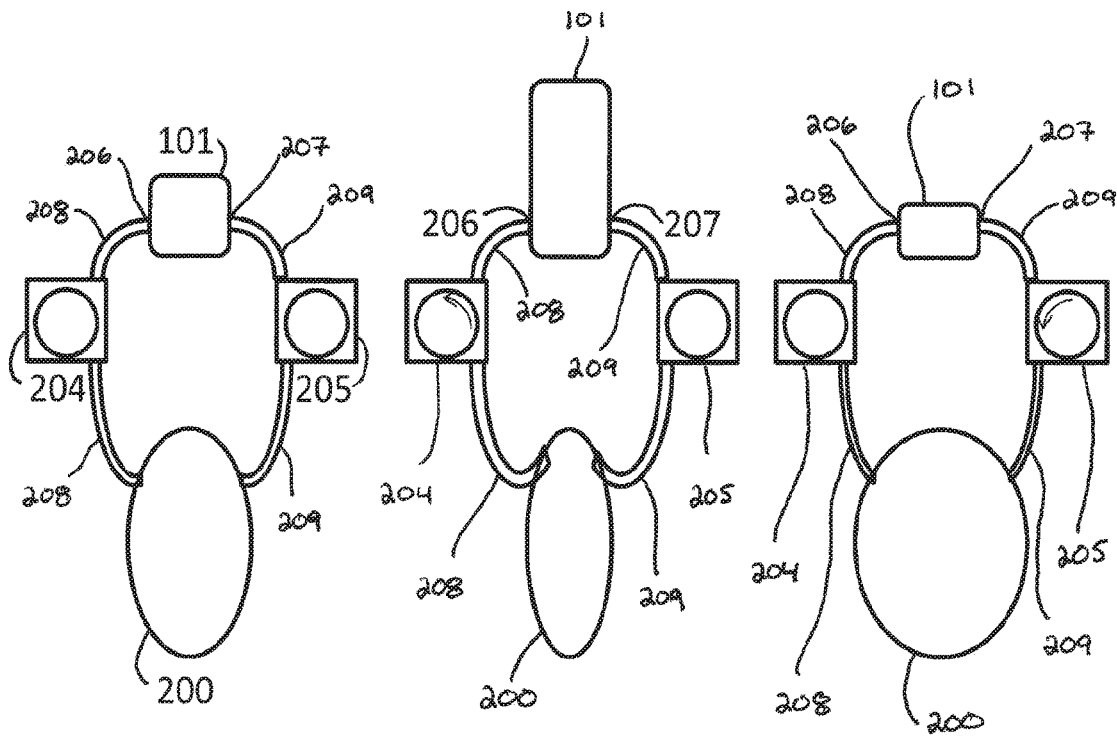
FIGS. 2a-2c are schematic diagrams that illustrate the use of two pumps to control bladder volume according to an embodiment of the present disclosure.
Figure 3:
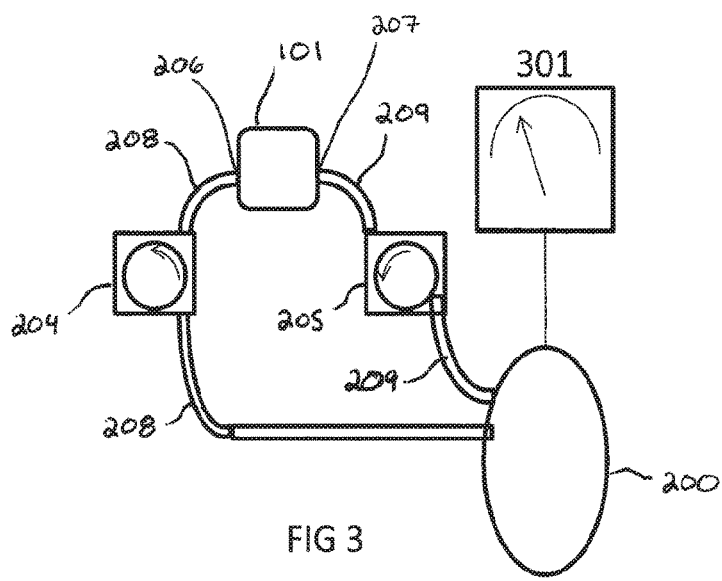
FIG. 3 is a schematic diagram that illustrates a system and/or method for measuring volume of fluid in a reservoir.

The bladder 101 may include one or more openings or valves to facilitate the passage of fluid therethrough. One or more pumps may facilitate such movement of the fluid. For example, as shown in FIGS. 2a-3, the bladder 101 may be equipped with egress and ingress ports 206 and 207, which allow for the flow of fluid into and out of the space enclosed by the bladder 101. The egress and ingress ports 206 and 207 may be operatively or directly connected to fluids paths 208 and 209, which in turn can be connected to a reservoir of fluid 200 (e.g., a bag). Each of the two fluid paths 208, 209 may run through a one way pumping system 204 and 205, such as, but not limited to, a positive displacement pump, a roller pump or a peristaltic pump. In one embodiment, each fluid path 208, 209 may only run through one of the two pumps 204, 205.

The pumps 204, 205 may be arranged so that activating one of them (e.g., pump 205) pulls fluid from the reservoir 200 and sends it into the bladder 101 and the other (e.g., pump 204) pulls fluid from the bladder 101 and sends it to the reservoir 200. In such an embodiment, if both pumps 204, 205 are activated at the same time and at the same speed (e.g., rate), then the amount of fluid flowing out of the reservoir 200 and into the bladder 101 will be the same as the amount of fluid flowing into the reservoir 200 and out of the bladder 101. Such operation will result in a static volume of fluid in the bladder 101 that flows continuously through the bladder 101, thereby allowing heat to be removed from the vicinity of the transducer 100b.

If the pump 205 pulling fluid from the reservoir 200 operates a greater speed relative to the pump 204 pulling fluid from the bladder 101, then the volume of fluid in the bladder 101 will increase (see FIG. 2b) while fluid flows continuously through the space created by the bladder 101. During such an operation, a depth 107 of the focal point 100c decreases, as shown in FIG. 1c. Alternatively, if the pump 205 pulling fluid from the reservoir 200 operates at a lesser speed relative to the pump 204 pulling fluid from the bladder 101, then the volume of fluid in the bladder 101 will decrease (see FIG. 2c) while fluid flows continuously through that volume. During such an operation, the depth 105 of the focal point 100c increases, as shown in FIG. 1a. Similarly, an intermediate depth 106 of the focal point 100c may be obtained by varying operation of the pumps 204, 205. As understood by those of ordinary skill in the art, depth 106 is less than depth 105, but greater than depth 107.

In one embodiment of the present disclosure, the two pumps 204, 205 are connected electronically to a control system, such as a computer or a switch box, capable of turning on/off the pumps 204, 205 independently through user input via a keyboard, mouse, touchscreen, and/or hard wired buttons, for example. Alternatively, the pumps 204, 205 can be activated manual. In a further embodiment as shown in FIG. 3, the reservoir 200 can be hung from or positioned on top of a system capable of measuring weight, such as a scale 301. Such a system may be used to determine if the net flow of water is in or out of the space defined by the bladder 101.

In one method of operation, the FUS probe 100 with the distensible bladder 101 enclosing the transducer end of the probe 100 is inserted into or against a region of tissue of a patient to be treated. The bladder 101 may have two tubes 208, 209 or conduits or pathways connecting the bladder 101 to a fluid reservoir 200. Each of the tubes 208, 209 may run through a pump 204, 205 capable of causing fluid to flow through the respective tube 208, 209.

The bladder 101 may be positioned at least partially or entirely between the transducer 100b and the tissue to be treated. Once the probe 100 is positioned proximate to or against the tissue to be treated, the correct location of the focal spot 100c within the tissue can be adjusted by varying the amount of fluid in the bladder 101. Fluid is added to the bladder 101 so that it increases in size by activating the pump 205 at a speed greater than the pump 204, thereby causing fluid to flow from the reservoir 200 into the bladder 101. Fluid may be removed from the bladder 101 so that it decreases in size by activating the pump 204 at a speed greater than the pump 205, thereby causing fluid to flow into the reservoir 200 from the bladder 101. Once the bladder 101 is filled to the desired volume, the two pumps 204, 205 can be run at the same speed in order to keep the volume constant and to circulate continuously fluid in order to remove heat from the transducer(s) 100b.

In a further embodiment, one or more feedback mechanisms may be included that allow the volume of fluid in the bladder 101 to be determined directly or indirectly. As a direct measure, medical imaging can be performed on the system in order to determine the distance of the transducer 100b from the desired focal spot. The distance has a direct relationship on the volume of fluid contained within the bladder 101. Greater precision can be obtained by measuring the weight of fluid in the reservoir 200. This can be realized by suspending the reservoir 200 from a hook attached to a scale 301 (see FIG. 3) or resting the reservoir 200 on a scale 301. By using a feedback loop where the reading from the scale 301 is fed into the system controlling the activation and flow rates of the two pumps 204, 205, very small amounts of fluid can be added to or removed from the reservoir 200 in order to maintain the volume of fluid contained within the bladder 101 at a fixed level or a targeted different level.

Figure 4:
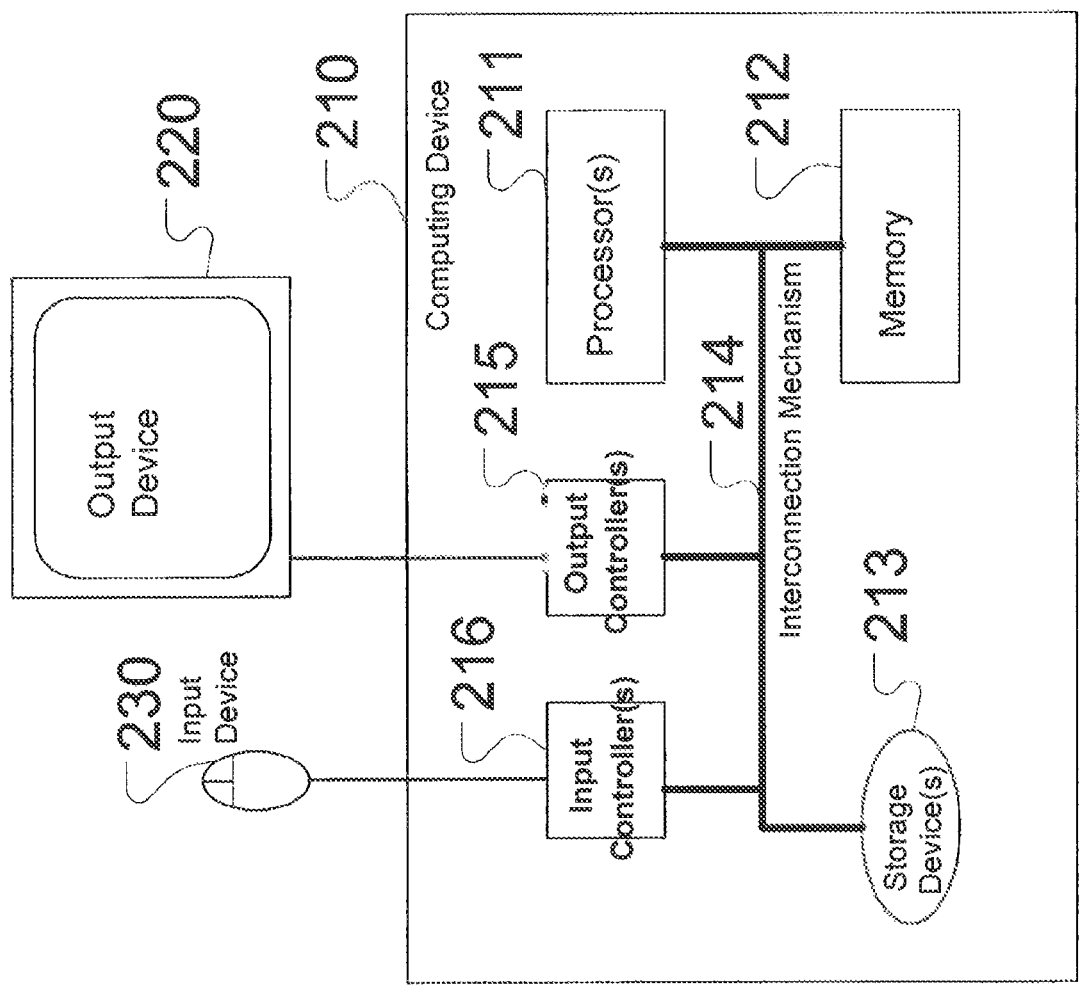
FIG. 4 is a schematic diagram of an exemplary computing device useful for performing at least certain processes disclosed herein.

One or more of the above-described techniques and/or embodiments may be implemented with or involve software, for example modules executed on or more computing devices 210 (see FIG. 4). Of course, modules described herein illustrate various functionalities and do not limit the structure or functionality of any embodiments. Rather, the functionality of various modules may be divided differently and performed by more or fewer modules according to various design considerations.

Each computing device 210 may include one or more processing devices 211 designed to process instructions, for example computer readable instructions (i.e., code), stored in a non-transient manner on one or more storage devices 213. By processing instructions, the processing device(s) 211 may perform one or more of the steps and/or functions disclosed herein. Each processing device may be real or virtual. In a multi-processing system, multiple processing units may execute computer-executable instructions to increase processing power. The storage device(s) 213 may be any type of non-transitory storage device (e.g., an optical storage device, a magnetic storage device, a solid state storage device, etc. The storage device(s) 213 may be removable or non-removable, and may include magnetic disks, magneto-optical disks, magnetic tapes or cassettes, CD-ROMs, CD-RWs, DVDs, BDs, SSDs, or any other medium which can be used to store information. Alternatively, instructions may be stored in one or more remote storage devices, for example storage devices accessed over a network or the internet.

Each computing device 210 additionally may have memory 212, one or more input controllers 216, one or more output controllers 215, and/or one or more communication connections 240. The memory 212 may be volatile memory (e.g., registers, cache, RAM, etc.), non-volatile (e.g., ROM, EEPROM, flash memory, etc.), or some combination thereof. In at least one embodiment, the memory 212 may store software implementing described techniques.

An interconnection mechanism 214, such as a bus, controller or network, may operatively couple components of the computing device 210, including the processor(s) 211, the memory 212, the storage device(s) 213, the input controller(s) 216, the output controller(s) 215, the communication connection(s) 240, and any other devices (e.g., network controllers, sound controllers, etc.). The output controller(s) 215 may be operatively coupled (e.g., via a wired or wireless connection) to one or more output devices 220 (e.g., a monitor, a television, a mobile device screen, a touch-display, a printer, a speaker, etc.) in such a fashion that the output controller(s) 215 can transform the display on the display device 220 (e.g., in response to modules executed). The input controller(s) 216 may be operatively coupled (e.g., via a wired or wireless connection) to an input device 230 (e.g., a mouse, a keyboard, a touch-pad, a scroll-ball, a touch-display, a pen, a game controller, a voice input device, a scanning device, a digital camera, etc.) in such a fashion that input can be received from a user.

The communication connection(s) 240 may enable communication over a communication medium to another computing entity. The communication medium conveys information such as computer-executable instructions, audio or video information, or other data in a modulated data signal. A modulated data signal is a signal that has one or more of its characteristics set or changed in such a manner as to encode information in the signal. By way of example, and not limitation, communication media include wired or wireless techniques implemented with an electrical, optical, RF, infrared, acoustic, or other carrier.

FIG. 4 illustrates the computing device 210, the output device 220, and the input device 230 as separate devices for ease of identification only. However, the computing device 210, the display device(s) 220, and/or the input device(s) 230 may be separate devices e.g., a personal computer connected by wires to a monitor and mouse may be integrated in a single device (e.g., a mobile device with a touch-display, such as a smartphone or a tablet), or any combination of devices (e.g., a computing device operatively coupled to a touch-screen display device, a plurality of computing devices attached to a single display device and input device, etc.). The computing device 210 may be one or more servers, for example a farm of networked servers, a clustered server environment, or a cloud services running on remote computing devices.

Therefore, the present invention is well adapted to attain the ends and advantages mentioned as well as those that are inherent therein. While numerous changes may be made by those skilled in the art, such changes are encompassed within the spirit of this invention as illustrated, in part, by the appended claims.

What is claimed is:

1. A system for providing focused ultrasound, the system comprising:
   a focused ultrasound probe including at least one transducer;
   at least one variable volume fluid bladder positioned proximate at least a portion of the transducer, the at least one bladder including an ingress port spaced-apart from an egress port;
   a reservoir;
   a first conduit extending from the reservoir to the ingress port of the at least one bladder;
   a second conduit extending from the egress port of the at least one bladder to the reservoir, the second conduit being separate from the first conduit;
   a first pump operatively connected to the at least one bladder and the reservoir, the first conduit extending through the first pump, the first pump being configured to move fluid from the reservoir and into the at least one bladder through the ingress port; and
   a second pump operatively connected to the at least one bladder and the reservoir, the second conduit extending through the second pump, the second pump being configured to move fluid out of the at least one bladder through the egress port and into the reservoir.

2. The system according to claim 1, further comprising at least one processor configured to vary an operating speed of at least one of the first and second pumps to increase or decrease a volume of fluid within the at least one bladder.

3. The system according to claim 2, wherein the operating speed of each of the first and second pumps is automatically controlled by the at least one processor that executes a predetermined treatment plan.

4. The system according to claim 3, the at least one processor automatically adjusts the operating speed of at least one of the first and second pumps to compensate for changes in a tissue volume.

5. The system according to claim 1, wherein at least one processor is configured to adjust an operating speed of at least one of the first and second pumps to compensate for changes in a tissue volume.

6. The system according to claim 1, wherein at least a portion of the at least one bladder is fixed to at least a portion of the at least one transducer.

7. The system according to claim 1, wherein the at least one bladder is in contact with at least a portion of the at least one transducer.

8. The system according to claim 1, wherein the reservoir is hung from or positioned on top of a scale.

9. The system of claim 1, wherein the system forms a single fluid loop from a fluid outlet of the reservoir, through the first pump, into the ingress port of the at least one bladder, out the egress port of the bladder, through the second pump, and into a fluid inlet of the reservoir.

10. The system of claim 1, wherein the reservoir includes a fluid inlet and a fluid outlet, the fluid outlet being spaced-apart from the fluid inlet.

11. The system of claim 1, wherein the system consists essentially of:
   the focused ultrasound probe including the at least one transducer;
   the at least one variable volume fluid bladder including the ingress port spaced-apart from the egress port;
   the reservoir;
   the first conduit extending from the reservoir to the ingress port of the at least one bladder;
   the second conduit extending from the egress port of the at least one bladder to the reservoir;
   the first pump; and
   the second pump.

12. A method of delivering focused ultrasound treatment, the method comprising:
   placing a variable volume fluid bladder between at least a portion of a transducer of a focused ultrasound device and tissue to be treated, the bladder including an ingress port spaced-apart from an egress port, a first conduit extending from a reservoir containing fluid to the ingress port of the bladder, a second conduit extending from the egress port of the bladder to the reservoir, the second conduit being separate from the first conduit, the first conduit extending through a first pump, the second conduit extending through a second pump;
   drawing fluid, via the first pump, from the reservoir and into the bladder through the ingress port;

drawing fluid, via the second pump, from the bladder through the egress port and into the reservoir; and varying an operating speed of at least one of the first pump and the second pump to (i) control circulation of fluid around or near at least a portion of the transducer and (ii) adjust a position of a focal spot of the transducer.

13. The method according to claim 12, further comprising:

operating the first pump and the second pump at substantially the same speed to (i) maintain a relatively constant volume of fluid in the bladder and (ii) continuously circulate fluid to remove at least some heat from the focused ultrasound device.

14. The method according to claim 12, further comprising:

measuring weight of fluid in the reservoir to control operation of at least one of the first and second pumps.

15. The method according to claim 12, further comprising:

automatically adjusting, via at least one processor, the operating speed of at least one of the first and second pumps to compensate for changes in tissue volume.

16. The method according to claim 12, further comprising:

automatically controlling, via at least one processor, the operating speed of at least one of the first pump and the second pump to execute a predetermined treatment plan.

17. A system for providing focused ultrasound, the system comprising:

a focused ultrasound probe including a transducer;

a variable volume fluid bladder surrounding at least a portion of the transducer, the bladder including an ingress port spaced-apart from an egress port;

a reservoir including a fluid inlet and a fluid outlet, the fluid outlet being spaced-apart from the fluid inlet;

a first pump connected to the fluid outlet of the reservoir and the ingress port of the bladder, the first pump being configured to move fluid from the reservoir through the fluid outlet thereof and into the bladder through the ingress port thereof; and a second pump connected to the egress port of the bladder and the fluid inlet of the reservoir, the second pump being configured to move fluid out of the bladder through the egress port and into the reservoir through the fluid inlet thereof.

18. The system of claim 17, wherein the system forms a single fluid loop from the fluid outlet of the reservoir, through the first pump, into the ingress port of the bladder, out the egress port of the bladder, through the second pump, and into the fluid inlet of the reservoir.

19. The system of claim 18, further comprising:

a first conduit extending from the fluid outlet of the reservoir to the ingress port of the bladder, the first conduit extending through the first pump; and a second conduit extending from the egress port of the bladder to the fluid inlet of the reservoir, the second conduit being separate from the first conduit, the second conduit extending through the second pump.

* * * * *